(12) United States Patent
Virtanen et al.

(10) Patent No.: US 8,030,054 B2
(45) Date of Patent: Oct. 4, 2011

(54) REACTOR AND METHOD FOR SOLID STATE FERMENTATION

(75) Inventors: Veera Virtanen, Espoo (FI); Seppo Jääskeläinen, Helsinki (FI); Pekka Seiskari, Luoma (FI)

(73) Assignee: Verdera Oy (FI)

( * ) Notice: Subject to any disclaimer, the term of this patent is extended or adjusted under 35 U.S.C. 154(b) by 508 days.

(21) Appl. No.: 11/576,195

(22) PCT Filed: Sep. 27, 2005

(86) PCT No.: PCT/FI2005/000408
§ 371 (c)(1), (2), (4) Date: Jul. 9, 2007

(87) PCT Pub. No.: WO2006/035104
PCT Pub. Date: Apr. 6, 2006

(65) Prior Publication Data
US 2008/0057576 A1    Mar. 6, 2008

(30) Foreign Application Priority Data
Sep. 28, 2004 (FI) ..................... 20041253

(51) Int. Cl.
*C12N 1/14* (2006.01)
(52) U.S. Cl. ............... 435/256.8; 435/255.7; 435/173.1; 435/303.3; 435/309.1
(58) Field of Classification Search ............ None
See application file for complete search history.

(56) References Cited

U.S. PATENT DOCUMENTS

| 4,803,800 A | * | 2/1989 | Romaine et al. ............ 47/1.1 |
| 5,159,694 A | | 10/1992 | Overath et al. |
| 6,558,943 B1 | | 5/2003 | Li et al. |

FOREIGN PATENT DOCUMENTS

| CN | 1 473 924 | 2/2004 |
| EP | 1 073 708 | 2/2001 |
| JP | 63-087972 | 4/1988 |
| JP | 63-283571 | 11/1988 |
| JP | 2003 088837 | 3/2003 |

OTHER PUBLICATIONS

International Search Report; PCT/FI2005/000408; Jan. 25, 2006.
Written Opinion of the International Searching Authority; PCT/FI2005/000408; Jan. 25, 2006.
Reply to Written Opinion; International Patent Application PCT/FI2005/000408; Jul. 28, 2006.
International Preliminary Report on Patentability; PCT/FI2005/000408; Nov. 15, 2006.
English Translation of Japanese Office Action, JP Patent Application No. 532913/2007, Oct. 19, 2010.

* cited by examiner

*Primary Examiner* — Jim Ketter
(74) *Attorney, Agent, or Firm* — Cantor Colburn LLP

(57) ABSTRACT

This invention describes a method for cultivating micro-organisms on solid growth medium in a solid state fermenting reactor by utilising external vibration for transportation and even inoculation of the solid growth medium. The reactor to be used is realized by attaching an external vibrator and at least one inoculation feed inlet to its outer wall.

12 Claims, 2 Drawing Sheets

REACTOR AND METHOD FOR SOLID STATE FERMENTATION

TECHNICAL FIELD OF INVENTION

The present invention relates to a solid state fermentation reactor and to the method of using this reactor for cultivating microorganisms on solid growth medium.

BRIEF DISCUSSION OF RELATED ART

Solid state fermentation (SSF) is well known to a person skilled in the art as a method for cultivating microbes on media where water is impregnated to a solid carrier. The amount of free water is very small contrary to submerged liquid fermentation.

Traditionally SSF has been used in applications where strict asepsis has not been required. Bulky media such as cereal grains, compost, granular clay or vermiculite are commonly used. However, production of novel biotechnical products and microbial inoculants need complete asepsis. Also more sophisticated and defined growth media have been developed and applied as described in WO 9218623.

So far, even novel applications of SSF have still relied on traditional process technology: fermentation is made on culture medium spread on growing trays which are placed on shelves in a closed chamber. Cultivation in plastic bags or pots is also used. Such routines require abundant manual labor and are slow. The capacities of these types of reactors are small due to dead space inside the reactors.

Various types of reactors for growing microbes on solid culture media have been developed for solid state fermentations as shown by Mitchell et al., Process Biochemistry (2000) 1211-1225. These include packed bed reactors, rotating drum reactors, gas-solid fluidized bed reactors and reactors wherein mixers of different kind (see US-patent publication 2002031822) have been used.

In aseptic solid state cultivations, even and aseptic distribution of the inoculum throughout the whole medium is essential. Tray reactors are commonly inoculated after sterilization by spraying inoculum liquid on the surface of the medium on each shelf or by immersing the whole content of the reactor in suspension containing the desired microbe and draining the excess liquid. More complex mixed packed bed reactors are expensive and difficult to operate aseptically.

In non-aseptic cultivations inoculation is much easier to control since occasional contaminating microbes do not create problems. The inoculum can be introduced in solid or liquid form to the growth medium on growing trays or continuously on a conveyor belt (mushroom spawn). In some applications the inoculation is made by dried spore powder blown on the medium with air.

Traditional solid fermentation process technology is difficult and laborious to apply to modern biotechnical processes where strict asepsis is required. In tray reactors the dead space is about one half of the bioreactor volume. The bioreactor size needed for particular product yield is therefore remarkably smaller in packed bed than in tray bioreactors, which make the tray type bioreactor less efficient. The operation of tray bioreactors needs also a lot of manual labor, because each tray has to be filled, emptied and cleaned individually.

By contrast, the packed bed bioreactor is easy to fill and empty by pouring the culture medium in and out and cleaning is also simple. The packed bed bioreactor is thus more cost, labor and space effective than the tray bioreactor. The drawback in packed bed reactors has been the inoculation.

Reactors with mixers have been developed for modern SSF applications but aseptic mixing device equipped with motors are very expensive. Mechanical abrasion in mixing can also damage the airy, loose structure of the growth medium when certain sensitive carriers are used. Rotating drum reactors can provide sufficient mixing only for solid growth media having certain kind of freely rolling structure.

Even novel solid fermentations are still made using complex, bulky media such as cereal grains supplemented with various flours. Optimal control of growth conditions and product formation can be achieved on more defined media which can be sensitive to mixing or to immersing completely in liquid.

The invention introduces a new type of packed bed solid state fermenting device for performing aseptic cultivations of pure cultures.

BRIEF SUMMARY OF INVENTION

The invention further aseptically and uniformly inoculates any kind of solid growth medium at high volumes.

Additionally, the invention provides a simplified, easy-to-use and cost-effective reactor and process for aseptic cultivations.

It was found that by using external vibration on the sterile solid growth medium inside a reactor the medium could be aseptically and controllably moved or transferred inside the reactor towards the point of inoculation and beyond, and simultaneously evenly inoculated with a pure culture.

DETAILED DESCRIPTION OF THE INVENTION

According to the method of the invention the solid growth medium inside the solid state fermenting (SSF) reactor, to be used for cultivation of micro-organisms is transferred by means of external vibration from the initial position of rest towards the point of inoculation and beyond. When a controlled mass flow of the solid growth media passes the point of inoculation it will be uniformly and continuously inoculated.

The solid growth medium comprises various organic or inorganic carriers, which can be moved by vibration. The inorganic carriers are preferably such as vermiculite, perlite, amorphous silica or granular clay. These types of materials are commonly used because they form loose, airy granular structure having preferably a particle size of 0,5-50 mm and a high surface area. The organic carriers are preferably such as cereal grains, bran, sawdust, peat or wood chips.

In addition, the solid growth medium may contain supplemental nutrients for the microorganism. Typically, these include carbon sources such as carbohydrates (sugars, starch), proteins or fats, nitrogen sources in organic form (proteins, amino acids) or inorganic nitrogen salts (ammonium and nitrate salts, urea), trace elements or other growth factors (vitamins, pH regulators). The solid growth medium may contain aids for structural composition, such as super absorbents, for example polyacrylamides.

Figure 2:
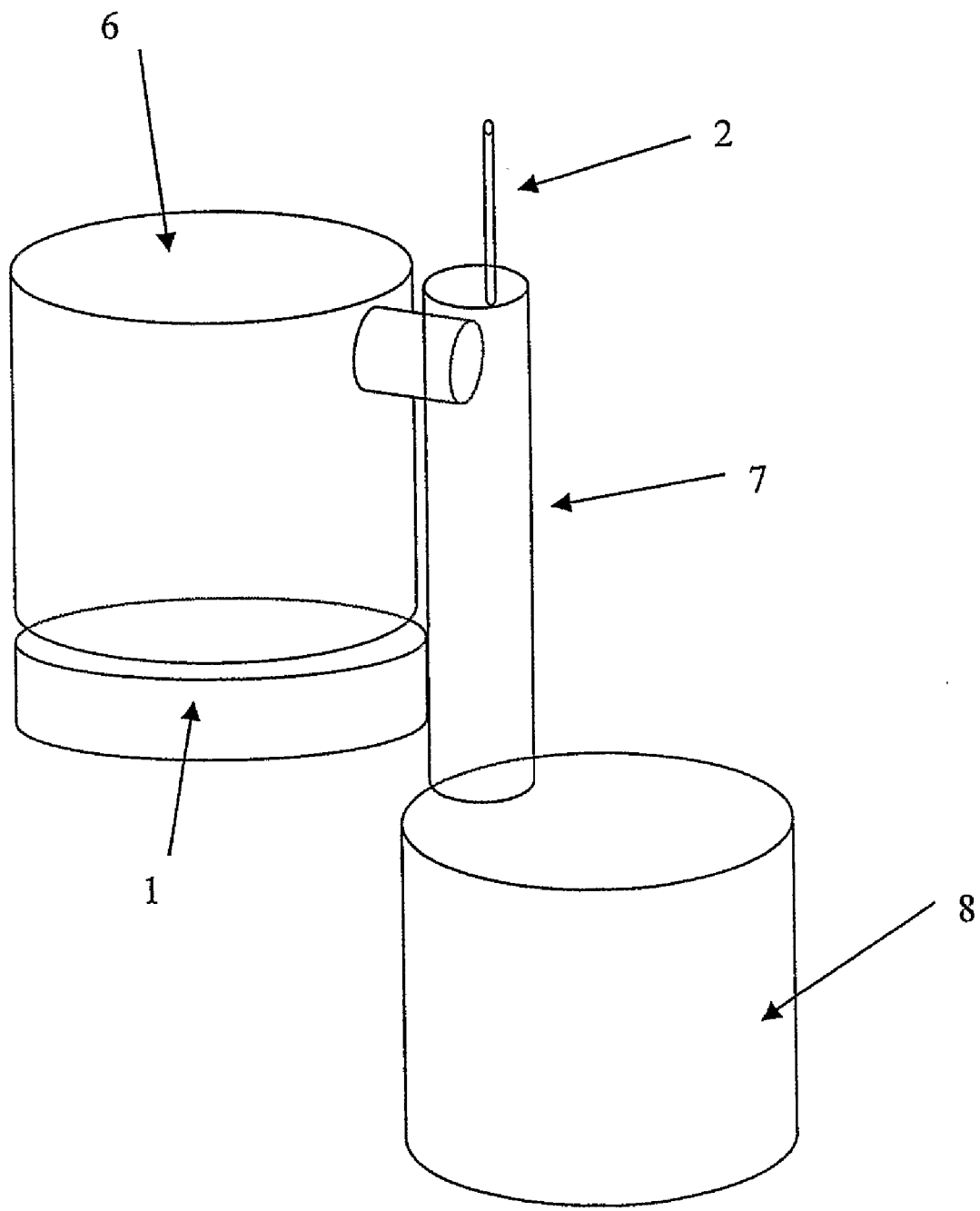
FIG. 2 describes a reactor layout according to the invention comprising a vibrator 1, an inoculum feed inlet 2, a medium sterilizing unit 6, a down corner tube 7 and a growth vessel 8.

According to one preferred embodiment of the invention the solid growth medium inside the medium sterilizing unit is sterilized ex situ. For example, a vibrating spiral feed vessel (as shown in FIG. 2) can be detached from the reactor body, filled with solid growth medium and sterilized in e.g. an autoclave, after which it can again be attached to the reactor body aseptically before starting the operation (vibration and inoculation).

In another preferred embodiment the solid growth medium inside the medium sterilizing unit is sterilized in situ before starting the inoculation e.g. with the aid of steam.

The microorganism to be cultivated and inoculated on the solid growth medium comprises fungi, including yeasts, for example such as *Phlebiopsis gigantea, Gliocladium* sp., *Nectria pityrodes, Chondrostereum purpureum, Pseudozyma flocculosa, Coniothyrium minitans, Trichoderia* sp.,*Metarrhizium* sp.,*Verticillium* sp . or *Beauveria bassiana*. Preferably the fungi are *Phlebiopsis gigantea, Gliocladium catenulatum, Nectria pityrodes* or *Chondrostereum purpureum*. The fungi additionally include edible mushrooms such as *Agaricus bisporus, Lentinus edodes* or *Pleurotus ostreatus*. The microorganism according to the invention can be bacteria such as *Streptomyces* sp., *Bacillus thuringiensis*, other *Bacillus* sp . or *Pseudomonas*sp. , preferably *Streptomyces*sp . In addition, nematodes could be used as microorganism to be grown according to the invention.

The inoculum is fed to the reactor according to the invention in liquid or solid form, preferably liquid.

If liquid media is used as inoculum it can be in the form of for example suspension with a small particle size to enable the use of spraying techniques. Preferably, the liquid media is sprayed on a continuous stream of the solid growth medium passing the point of inoculation.

If the inoculum is in solid form it can be transported to the point of inoculation similarly to transporting the solid growth medium, by vibration. Preferably, the solid inoculum is transported using a screw, vibrator or belt conveyor. This ensures that the microorganism can be transported equally aseptically for cultivation.

The external vibration is achieved by conventional vibration means by attaching a vibrator to the reactor outer body. Preferably, the vibration is generated by external electric rotary vibrators, magnetic, hydraulic or pneumatic vibrators. Most preferably, an electric rotary vibrator is used.

The reactor of the invention is defined as stated in the independent claim.

There can be several different constructions to realize the functionality of the invention, the placement of the vibration mean(s) and the reactor entities or units.

Figure 1:
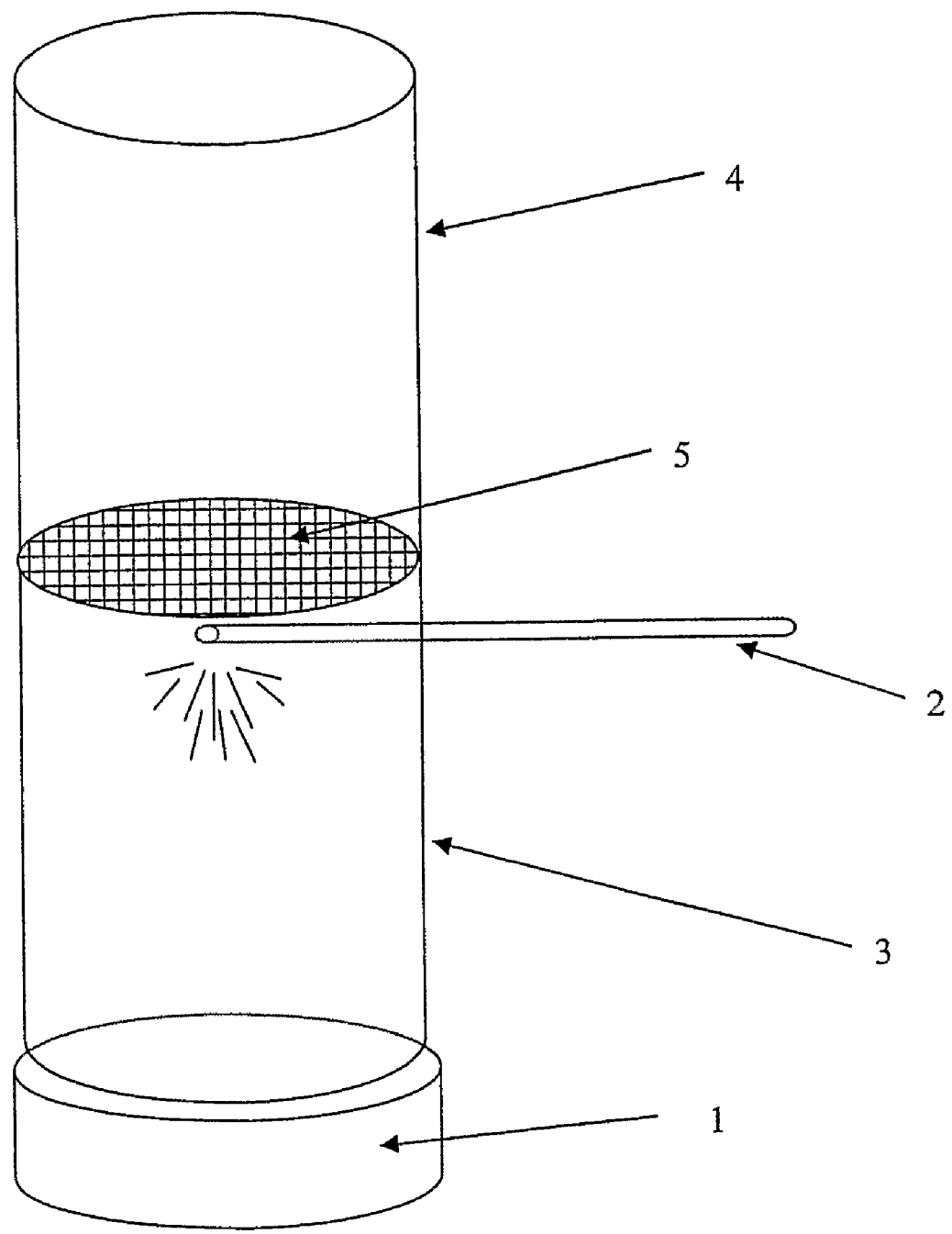
FIG. 1 describes a reactor layout according to the invention comprising a vibrator 1, an inoculum feed inlet 2, a reactor lower compartment 3, a reactor upper compartment 4 and a screen 5.

In one preferred embodiment according the invention the reactor body comprises at least four entities as shown in FIG. 1. There are two main compartments, an upper compartment 4 and a lower compartment 3, separated from each other by a permeable separator 5, and an external vibrator 1 is attached to the outer wall of the reactor body. At least one inlet 2 is attached to the lower compartment for inoculation. This reactor body is optionally turnable upside down and thus includes means for turning.

The shape and size of the reactor compartments may vary depending on the need of the cultivation and used materials. The shape needs even not to be restricted to well defined shapes, but could be mouldable or plastic like. Preferably, the shapes of the vessels are cylindrical, angular or conical.

According to the invention the permeable separator facilitates a regulated and homogenous flow of the solid growth medium towards the point of inoculation with the aid of vibrator after the reactor compartment has been filled and turned upside down. The shape of the permeable separator may vary depending on the flow rate required for the solid growth medium through the separator. Preferably, the permeable separator is a screen or a perforated plate. The aperture size of the separator depends on the structure and particle size and shape of the solid growth medium and is preferably 5-50 mm.

The permeable separator can be a static one, fixed at a predetermined position thus dividing the reactor compartment into fixed volumes of the upper compartment 4 and the lower compartment 3. The operation of the reactor for this preferred embodiment requires the reactor body to be turned upside down after filling the reactor and sterilising the solid growth medium therein. The turning is realized either manually or automatically, with the aid of a lifting device.

Another alternative is a moving separator in which case the volume ratio of the compartment 4 to compartment 3 can be adjusted. The separator can be moved e.g. by attaching it to a rotating screw, which is turnable from outside.

In another preferred embodiment according the invention the reactor body comprises an external vibrator 1 connected to a detachable solid growth medium sterilizing unit 6, which is attached to a down corner tube 7. To a suitable part of this reactor body, at least one inoculation feed inlet 2 is connected in order to achieve an even and continuous inoculation of the solid growth medium. The down corner tube 7 is connected to a growth vessel 8 wherein the cultivation takes place after the inoculation.

Preferably, the down corner tube is a flexible one to adopt the movement of the vibrating medium sterilizing unit.

The detachable solid growth medium sterilizing unit 6 is advantageous since its dead volume during sterilization is minimal. If detached for sterilization it is subsequently aseptically reattached to the reactor body. Preferably, the medium sterilizing unit 6 is a vibrating spiral feed vessel.

The shape of the reactor body units can vary, but are preferably cylindrical, angular or conical.

So far, commercial scale aseptic packed bed bioreactors have not been available. The biggest challenge has been homogenous inoculation, especially with media, which do not tolerate vigorous mixing. The reactor and the method for using it according to the invention are able to overcome these problems associated with invasive moving of solid growth medium. Mixing device inside the reactor causes a risk of channelling of aeration air in the area surrounding the mixer. Vigorous mixing may cause mechanical reshaping the growth medium (e.g. loss of looseness).

In the present invention the solid growth medium is transferred aseptically through a screen or from one vessel to another by vibrating it with an external vibrator. At the same time the inoculum is fed to the solid growth medium. This method is simple and aseptic and requires no mixing of culture medium.

The invention is illustrated in the following examples without limiting the scope defined by the claims.

EXAMPLE 1.

*Phlebiopsis gigantea* (Rotstop, trademark of Verdera Oy) was grown using the packed bed solid state reactor on a silica based solid growth medium using a reactor layout shown in FIG. 1.

Nutrient solution suitable for *P. gigantea* was prepared by dissolving 9 kg of condensed distiller's grain (Altia Oyj) to 33 kg of tap water. The solution was impregnated to 15 kg of amorphous silica powder (Degussa) by mixing for 3 minutes in a dough mixer to form a granular growth medium. 700 g of lime was added prior to mixing to control the pH.

The fermenting reactor was loaded with the culture medium uptil a static screen, aperture size 1 cm, placed in the middle of the reactor. The reactor was sealed and sterile filters were attached to the inlets. The reactor was sterilized in an autoclave for 1 h at 121° C. After autoclaving the reactor was let to cool down overnight.

*P. gigantea* inoculum was cultivated in shake flasks in malt-extract solution for 4 d at 28° C. The inoculum was homogenized before transferring it into the reactor. The solid growth medium was inoculated by manually turning the reactor upside down and vibrating it with an external pneumatic roller vibrator (Netter Vibrationstechnik GmbH). Vibrating caused the solid medium to fall evenly through the screen. Inoculum solution was aseptically sprayed to the falling medium through a nozzle. 100 ml of inoculum was sprayed in 4 kg of solid medium at a rate of about 5 ml/s using a hollow cone nozzle.

The fungus was cultivated for 10 days at a temperature of 28° C. and aeration rate of 0.3 1/min/kg of growth medium. After cultivation the fungus had grown and sporulated throughout the whole medium. The medium was removed from the reactor and dried at room temperature for 3 d on drying shelves.

The dried medium contained $1*10^7$ cfu/g (cfu=colony forming units) of *P. gigantea*. The viability of the dried product was as high as obtained with traditional SSF methods.

EXAMPLE 2.

*P. gigantea* was grown using the packed bed solid state fermenting reactor shown in FIG. 2.

The solid growth medium for *P. gigantea* was prepared as described in example 1.

A vibrating medium sterilizing unit comprising a spiral feed vessel was filled with 40 kg of the culture medium. The vessel was sealed and sterilized in an autoclave for 90 min at 121° C. and left cooling down overnight. The feed vessel was attached on a vibrator base (Tärylaite Oy) equipped with rotary electric vibrators and aseptically connected to a sterile cylindrical growth vessel using a flexible down corner. The feed vessel was vibrated causing the solid growth medium inside to flow steadily upwards along the feeding spiral. The inoculum was cultivated as described in example 1. The solid growth medium was inoculated by spraying about 2 liters of homogenized inoculum at a rate of 300 ml/min with a hollow cone nozzle to the medium falling through the down corner tube into the growth vessel. The inoculum was sprayed to the upper end of the down corner tube. Thus, the whole medium was evenly inoculated.

The cultivation, collection and drying of the final product was made as described in example 1. The dried medium contained $1*10^7$ cfu/g of *P. gigantea*.

EXAMPLE 3.

*Streptomyces sp.* (Mycostop, trademark of Verdera Oy) was grown as described in examples 1 and 2 using as solid growth medium corn steep solids (css) 0.62 kg, lactose 0.62 kg, lime 0.62 kg, amorphous silica 12 kg and tap water 28.8 kg. The bacterium was cultivated 7 d at 28° C.

The dried medium contained $6*10^8$ cfu/g and $1*10^9$ cfu/g of *Streptomyces* made according to examples 1 and 2, respectively.

EXAMPLE 4

*Gliocladium catenulatum* (GlioMix, trademark of Verdera Oy) was grown as described in example 1 using as solid growth medium condensed distiller's grain 0.53 kg, lime 60 g, amorphous silica 1.5 kg, tap water 3.4 kg. The fungus was cultivated 18 d at 22° C.

The dried medium contained $3*10^8$ cfu/g of *G. catenulatum*.

EXAMPLE 5

*P. gigantea* was grown using the packed bed solid state fermenting reactor shown in FIG. 2 equipped with two different kinds of growth vessels and inoculum feed inlets.

The solid growth medium for *P. gigantea* was prepared as described in example 1.

A vibrating medium sterilizing unit comprising a spiral feed vessel was filled with 70 kg of the culture medium. The vessel was sterilized and attached on a vibrator base as described in example 2. Two different kinds of growth vessels were aseptically connected to the sterilizing unit using a flexible down corner tube: angular box shaped vessels having height:width:depth ratios of 1) 1:1:1 and 2) 10:6:3. The growth vessels were inoculated 1) as described in example 2 and 2) using a wide angle flat spray nozzle placed to the lower end of the down corner tube inside the growth vessel.

Very even inoculation of the solid growth medium was obtained with all described configurations. The cultivation, collection and drying of the final product was made as described in example 1. The dried medium contained about $1*10^7$ cfu/g of *P. gigantea* in all cultivation batches.

REFERENCE EXAMPLE

*Phlebiopsis gigantea* (Rotstop, trademark of Verdera Oy) was grown on a silica based solid growth medium the way described in example 1, in a sylindrical packed bed solid state fermenter equipped with a helical ribbon mixer with an inlet into the reactor space from the bottom. The reactor was a pressure vessel and it was sterilised in situ with steam at 121° C. After sterilisation and cooling the reactor was inoculated by pouring the inoculum onto the growth medium through an inlet into the reactor at the top of the reactor and by switching on the mixer simultaneously. The growth medium used was observed to be very vulnerable to mixing. After 5 min, its loose, airy structure was lost during the inoculation and the product obtained became dough like.

It was not possible to process further the material thus obtained.

The invention claimed is:

1. A method for cultivating microorganisms on solid growth media particles in a solid state fermenting (SSF) reactor system, comprising:
    disposing the particles of the solid growth media at a first position of rest within a first portion of the reactor system, the first position of rest being disposed upstream of a point of inoculation;
    transferring a flow of particles of the solid growth medium individually and continuously from the position of rest disposed upstream of the point of inoculation, to and beyond the point of inoculation, and to a second position of rest within a second portion of the system by means, at least, of external vibration, the second portion of the system being disposed downstream of the point of inoculation;
    feeding inoculum to the solid growth medium at the point of inoculation; and
    performing a uniform and continuous inoculation of the of the particles of the solid growth medium via the transferring of the flow of particles.

2. The method according to claim 1, wherein the inoculation is performed aseptically.

3. The method according to claim 1, wherein the solid growth medium comprises organic carriers and/or inorganic carriers.

4. The method according to claim 3, wherein the organic carriers are selected from the group consisting of cereal grains, bran, sawdust, peat and wood chips.

5. The method according to claim 3, wherein the inorganic carriers are selected from the group consisting of vermiculite, perlite, amorphous silica and granular clay.

6. The method according to claim 1, wherein the microorganisms to be cultivated are fungi, including yeasts, bacteria or nematodes.

7. The method according to claim 1, wherein the vibration is generated with external electric rotary vibrators, magnetic, hydraulic or pneumatic vibrators.

8. The method according to claim 1, wherein the microorganism to be used in the inoculation is fed onto the solid growth medium in liquid or solid form.

9. The method according to claim 8, wherein the liquid inoculum of the microorganism is sprayed as a suspension using a nozzle.

10. The method according to claim 8, wherein the solid inoculum of the microorganism is fed onto the solid growth medium using screw, vibration or a belt conveyor.

11. Method of growing a pure culture, comprising:
disposing particles of a solid growth medium inside a SSF reactor system at a first position of rest disposed upstream of a point of inoculation; and
transferring the particles of the solid growth medium individually and continuously from the position of rest disposed upstream of the point of inoculation, to and beyond the point of inoculation, and to a second position of rest within a second portion of the system by means, at least, of external vibration, the second portion of the system being disposed downstream of the point of inoculation.

12. The method according to claim 1, wherein the distinct vessel volumes are defined by a screen disposed in one vessel or two distinct vessel bodies that are communicable with each other.

* * * * *